Figure 1:
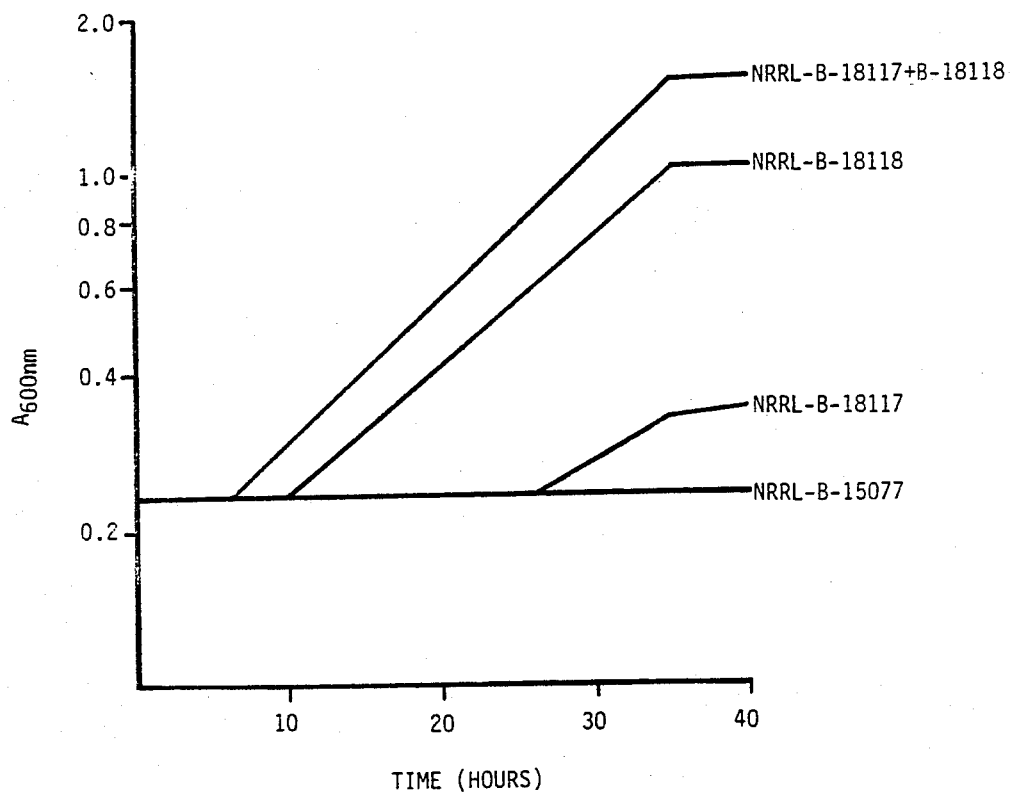

United States Patent [19]

Vandenbergh

[11] Patent Number: 4,910,143
[45] Date of Patent: Mar. 20, 1990

[54] BACTERIAL METHOD AND COMPOSITIONS FOR DEGRADING HYDROCARBONS

[75] Inventor: Peter A. Vandenbergh, Sarasota, Fla.

[73] Assignee: Microlife Technics, Inc., Sarasota, Fla.

[21] Appl. No.: 939,077

[22] Filed: Dec. 8, 1986

[51] Int. Cl.[4] ............... C12N 1/20; C12N 15/00; C12N 1/26

[52] U.S. Cl. ............... 435/252.34; 435/172.3; 435/248; 435/249; 435/262; 435/320; 435/877; 935/29; 935/56; 935/59; 935/72

[58] Field of Search .............. 435/172.3, 262, 248, 435/249, 320, 877; 935/56, 59, 72

[56] References Cited

U.S. PATENT DOCUMENTS

| | | | |
|---|---|---|---|
| 4,259,444 | 3/1981 | Chakrabarty | 435/172 |
| 4,452,894 | 6/1984 | Olsen et al. | 435/253 |
| 4,508,824 | 4/1985 | Olsen | 435/172.3 |
| 4,535,061 | 8/1985 | Chakrabarty et al. | 435/253 |
| 4,593,003 | 6/1986 | Vandenbergh | 435/172.3 |

OTHER PUBLICATIONS

Austen, R. A. et al; A Comparative Study of the NAH and TOL Catabolic Plasmids in *Pseudononas putida*; Aust. J. Biol. Sci. 30 (4) pp. 357–366.
White, G. P. et al; Compatibility and Sex Specific Phase Plating Characteristics of the TOL and NAH Catabolic Plasmids; Genet Res. 32(3) pp. 207–214 (1978).
Vandenbergh et al. Appl. Environ, Microbiol. 45: 1953–1955 (1983).
Vandenbergh, et al., Appl. Environ, Microbiol. 46: 128–132 (1983).
Vandenbergh et al., Appl. Environ, Microbiol. 52: 939–940 (1986).
Vandenbergh et al., Appl. Environ, Microbiol. 42: 737–739 (1981).
Stanier et al., J. Gen. Microbiol. 43: 159–271 (1966).
Olsen, J. Bacteriol. 133: 210–216 (1978).

*Primary Examiner*—Thomas D. Mays
*Attorney, Agent, or Firm*—Ian C. McLeod

[57] ABSTRACT

A mixture of *Pseudomonas putida* one having plasmids encoding the camphor (CAM) and toluene (TOL) degradation and the other having a plasmid encoding for naphthalene (NAH) degradation is described. The mixture is more effective than either *Pseudomonas putida* alone or than a single *Pseudomonas putida* with three related plasmids which encode for the degradation of CAM, TOL and NAH.

7 Claims, 1 Drawing Sheet

BACTERIAL METHOD AND COMPOSITIONS FOR DEGRADING HYDROCARBONS

BACKGROUND OF THE INVENTION

(1) Field of the Invention

The present invention relates to a bacterial method and compositions which utilize two (2) different plasmid modified strains of *Pseudomonas putida* together to more effectively degrade chemical compositions including mixed aliphatic and aromatic hydrocarbons, especially in the waste compositions. In particular, the present invention relates to a method and compositions which utilize a first *Pseudomonas putida* which contains first and second plasmids encoding for camphor (CAM) and toluene (TOL) degradation and a second *Pseudomonas putida* which contains a third plasmid which encodes for naphthalene (NAH) degradation as a result of mating of the plasmids into parent strains.

(2) Prior Art

Aliphatic and aromatic hydrocarbons are degraded in nature as shown in the following references: U.S. Pat. No. 4,452,894 to Olsen et al; U.S. Pat. No. 4,594,003 to Vandenbergh; Vandenbergh, P. A. and A. M. Wright, Appl. Environ. Microbiol. 45: 1953-1955 (1983); Vandenbergh, P. A., C. F. Gonzalez, A. M. Wright and B. S. Kunka, Appl. Environ. Microbiol. 46: 128-132 (1983); Vandenbergh, P. A., R. H. Olsen and J. F. Colaruotolo, Appl. Environ. Microbiol. 42: 737-739 (1981); and Vandenbergh, P. A., and R. L. Cole, Appl. Environ. Microbiol. 52: 939-940 (1986). The useful application of bacteria to the environment to degrade toxic waste has been previously demonstrated by U.S. Pat. No. 4,594,003. However, due to the complex nature of chemical waste sites many hydrocarbons are present and it is difficult to provide a mixture of many different strains having individual hydrocarbon degrading characteristics to handle a complex mixture of the hydrocarbons.

Through the use of bacterial genetics, it has been possible to improve the biochemical properties of hydrocarbon degrading strains and reduce the number of different strains by means of introduction of plasmids into the strains. Strains have been previously produced that contain multiple hydrocarbon degrading plasmids as shown by Chakrabarty et al U.S. Pat. No. 4,259,444. These modified strains grow slowly in a fermenter with subsequent poor growth yields in terms of numbers of bacteria per ml produced in the growth medium and thus are not practical to commercialize. Plasmid incompatibility and spontaneous curing of plasmids also reduce the utility of these strains.

OBJECTS

It is therefore an object of the present invention to provide a unique mixture of *Pseudomonas putida* strains which rapidly degrades chemical compositions particularly wastes found in the environment. Further it is an object of the present invention to provide a method for degrading the chemical compositions using this mixture. Further still it is an object of the present invention to provide strains of *Pseudomonas putida* which grow rapidly to high numbers per ml. These and other objects will become increasingly apparent by reference to the following description and the drawings.

IN THE DRAWINGS

FIG. 1 is a graph depicting the use of single strains of *Pseudomonas putida* and mixtures thereof and in particular showing the effectiveness of two (2) strains of *Pseudomonas putida* in mixtures where a fused CAM:TOL plasmid is provided in one strain and a NAH plasmid is provided in another strain.

GENERAL DESCRIPTION

The present invention relates to a bacterial composition for degrading aliphatic and aromatic hydrocarbons which comprises a mixture of: a *Pseudomonas putida* containing first and second plasmids encoding for camphor (CAM) and toluene (TOL) degradation; and a *Pseudomonas putida* containing a third plasmid encoding for naphthalene (NAH) degradation, wherein both of the *Pseudomonas putida* degrade aliphatic hydrocarbons, wherein the ratio of the *Pseudomonas putida* is between about 1:100 and 100 to 1 by cell count, and wherein the mixture degrades a chemical composition of naphthalene and camphor which can not be degraded as effectively by either of the *Pseudomonas putida* alone or by a single *Pseudomonas putida* containing two plasmids which encode for the degradation of both camphor and naphthalene. The strains are grown separately in substantially pure form and then combined.

The present invention also relates to a method for degrading aliphatic and aromatic hydrocarbons which comprises: providing a *Pseudomonas putida* containing first and second plasmids encoding for camphor (CAM) and toluene (TOL) degradation; and a *Pseudomonas putida* containing a third plasmid encoding for naphthalene (NAH) degradation wherein the *Pseudomonas putida* degrade aliphatic hydrocarbons, and, wherein the mixture degrades a chemical composition of naphthalene and camphor which can not be as effectively degraded by either of the *Pseudomonas putida* alone or by a single *Pseudomonas putida* with the plasmids which encode for the degradation of both naphthalene and camphor; and degrading the aliphatic and aromatic hydrocarbons.

The *Pseudomonas putida* can be grown in a growth medium containing yeast extract, dextrose, tryptone, potassium nitrate and sodium chloride. The yeast extract provides nitrogen and vitamins. Dextrose is a carbon source. The inorganic salts aid growth. Each strain grows to a level of about $10^{10}$ cells per ml. Normally *Pseudomonas putida* strains only grow to about $10^9$ cells per ml with multiple plasmids. The cells can be centrifuged from the growth medium to provide a concentrate containing between about $10^{11}$ and $10^{12}$ cells per ml. The cells can be frozen or lyophilized as is well known to those skilled in the art.

The preferred strains are *Pseudomonas putida* NRRL-B-18117 and 18118. These strains are deposited with the Northern Regional Research Laboratory in Peoria, Ill. under the Budapest Treaty and are available by number.

SPECIFIC DESCRIPTION

EXAMPLE 1

The following Example shows the derivation of the strains used.

The CAM:TOL fusion plasmid was mated with a frequency of $2.5 \times 10^4$ transconjugants/donor into the strain PPU4.0. Selection for the mating was direct with the hydrocarbon source being the only requirement in the minimal media. The NAH plasmid was mated into the strain PPU5.0, the transconjugant was able to utilize naphthalene and also grew well on hexane.

Bacterial Strains. The organisms and plasmids used in this study are listed in Table 1.

TABLE 1

List of Bacterial Strains

| Strains | Relevant Characteristics[a] |
|---|---|
| P. putida PPU4.0 | Prototroph |
| P. putida PPU5.0 | Prototroph |
| P. aeruginosa PAE1.23 | Arginine, leucine auxotroph $CAM^{+b}$, $TOL^+$ |
| P. putida PPU4.11 | Arginine auxotroph, $NAH^{+b}$ |
| P. putida PPU4.5(NRRL-B-18117) | $CAM^{+b}$, $TOL^+$ |
| P. putida PPU5.3(NRRL-B-18118) | $NAH^{+b}$ |

[a]CAM, camphor; TOL, toluene; NAH, naphthalene.
[b]Volatile carbon sources were supplied in the vapor phase in a sealed container. Incubation was for 48 h at 25° C.

Media. The pseudomonads in this study were grown only on minimal medium (mmo). (Stainier, R. Y., N. J. Palleroni and M. Doudoroff., J. Gen. Microbiol. 43: 159–271 (1966)). This media was then supplemented with the appropriate hydrocarbon source or amino acid as shown in Table 1.

Matings. Matings were accomplished by the method of Olsen (Olsen, R. H., J. Bacteriol. 133: 210–216 (1978)). The results are shown in Table 2.

TABLE 2

MATING FREQUENCIES

| DONOR | RECIPIENT | TRANSCONJUGANTS/ DONOR[a,b] |
|---|---|---|
| PAE1.23 × PPU4.0 | | PPU4.5 (2.5 × $10^4$) |
| PPU4.11 × PPU5.0 | | PPU5.3 (5.0 × $10^7$) |

[a]Selection was on minimal medium ($mm_o$) with the appropriate hydrocarbon source supplied in the vapor phase.
[b]Frequencies reported are the average of three different mating experiments.

Mutagenesis. The donors for the mating experiments were obtained through mutagenesis with 1-methyl-3-nitro-1-nitrosoguanidine (Sigma Chemical Co., St. Louis, MO.) by a procedure described by Vandenbergh et al (Vandenbergh, P. A., C. F. Gonzalez, A. M. Wright and B. S. Kunka, Appl. Environ. Microbiol. 46: 128–132 (1983)).

Growth. Table 3 shows the results of growth of each of the derived strains in a minimal media containing a single hydrocarbon source.

TABLE 3

Growth of Transconjugants on Additional Hydrocarbons

| | Cresol | | | | | | CRUDE | DIESEL | | HALO |
|---|---|---|---|---|---|---|---|---|---|---|
| | p | o | m | NAH | TOL | CAM | OIL | FUEL | PHENOL | AROMATICS |
| PPU4.5 | + | + | + | − | + | + | ++ | ++ | − | − |
| PPU5.3 | − | − | − | + | − | − | + | + | + | + |

[a]Volatile hydrocarbon sources were supplied in the vapor phase in a sealed container. Incubation was for 48 h at 25° C. +, growth; −, no growth.

EXAMPLE 2

This example shows the treatment of contaminated water from a chemical wood treatment processor. The strains were grown in the previously described growth medium to $10^{11}$ cells/ml, centrifuged to $10^{12}$ cells/ml and lyophilized.

The two strains of Pseudomonas putida were then placed into a solution containing 3.5% pentachlorophenol, diesel fuel, bunker "C" oil and cresol. These compounds require complex physiologies and one single strain is unable to grow in this composition.

A shake flask containing 20 ml of minimal media (MMo) and 20 ml of a mixture of pentachlorophenol/cresol/diesel fuel was used. The inoculation rate was $10^6$ of a 1:1 mixture of Pseudomonas putida NRRL-B-18117 (PPU 4.5) and NRRL-B-18118/ml (PPU 5.3). The flask was shaken at 250 rpm @ 25° C.

Total degradation of the mixture occurred in seven (7) days. The oily mixture disappeared and the flask contained $10^8$ bacteria/ml. It had been found that commercially available wastewater treatment strains did not degrade this chemical composition.

Each of the strains PPU 4.5 and PPU 5.3 possess broad chromosomal encoded traits and are useful in wastewater treatment. The additional supplementation of each strain with one plasmid, increased the number of degraded substrates and did not interfere with the growth of the strains.

EXAMPLE 3

This example shows the treatment of contaminated soil from a chemical wood treatment processor. The bacteria of Example 2 in an aqueous solution (about $10^9$ cells/ml) were sprayed onto the surface of soil contaminated with the same chemical composition as Example 2 and mixed with a bulldozer. The bacteria were applied every 3 days at $10^6$ (preferably between $10^3$ to $10^{10}$ cells per ml) bacteria/gram of soil. Six weeks after final application, the soil was free of these hydrocarbons.

EXAMPLE 4

Pseudomonas putida NRRL-B-18117 and Pseudomonas putida NRRL-B-18118 were inoculated separately and in combination into minimal media (mmo) supplemented with 0.3% camphor and 0.3% naphthalene. The flasks were shaken at 250 rpm and incubated at 25° C. Absorbance at 600 nm was recorded at various time intervals. Increased absorbance indicates larger numbers of bacteria per ml.

The results shown in FIG. 1 indicate that the combination of Pseudomonas putida NRRL-B-18118 and Pseudomonas putida NRRL-B-18117 were more successful in the utilization of the camphor and the naphthalene than the strains used separately. FIG. 1 also shows the results from using a strain, Pseudomonas putida NRRL-B-15077 containing multiple plasmids including a camphor plasmid and a naphthalene plasmid together. The results show poor growth of this strain on CAM and NAH in the minimal medium. Thus a single strain with multiple plasmids does not produce improved results.

EXAMPLE 5

Pseudomonas putida NRRL-B-18117 and Pseudomonas putida NRRL-B-18118, were inoculated at a rate of $10^6$ (preferably between $10^3$ to $10^{10}$ cells per ml) cells/ml into 30,000 gallons of waste material containing several organic compounds at different concentrations. The cultures were added (daily) for one week and the concentration of each of the organic compounds was determined using gas chromatography. The results are shown in Table 4.

TABLE 4

|  | Concentration Day zero (microgram/l) | Concentration Day seven (microgram/l) |
| --- | --- | --- |
| Methylene chloride | 1,500 | zero |
| Methyl ethyl ketone | 99,400 | 15,600 |
| Ethylacetate | 53,400 | zero |
| Methyl ethylacetate | 38,100 | zero |
| Cyclohexanone | 1,100 | zero |
| Methyl pentanone | 13,600 | 500 |
| Toluene | 20,700 | 400 |
| Ethylbenzene | 300 | zero |
| m-Xylene | 700 | <100 |
| o,p-Xylene | 700 | 100 |
| Butyl acetate | 6,800 | zero |
| Methyl propylacetate | 14,500 | 300 |

The results show that the combination of *Pseudomonas putida* NRRL-B-18117 and NRRL-B-18118 was very effective in degrading a wide variety of organic chemicals.

It is intended that the foregoing description be only illustrative of the present invention and that the present invention be limited only by the hereinafter appended claims.

I claim:

1. A bacterial composition which comprises a mixture of:
   (a) *Pseudomonas putida* strain NRRL-B-18117; and
   (b) *Pseudomonas putida* strain NRRL-B-18118 wherein the ratio of (a) to (b) is between about 1:100 and 100:1 by cell count.

2. A method for degrading aliphatic and aromatic hydrocarbons which comprises:
   contacting a substrate containing aromatic and aliphatic hydrocarbons with a bacterial composition which comprises *Pseudomonas putida* strain NRRL-B-18117 containing fused first and second plasmids encoding for camphor (CAM) and toluene (TOL) degradation; and *Pseudomonas putida* strain NRRL-B-18118 containing a third plasmid encoding for naphthalene (NAH) degradation wherein the *Pseudomonas putida* strains degrade aliphatic hydrocarbons, and wherein the *Pseudomonas putida* strains together degrade a chemical composition of naphthalene and camphor which can not be as effectively degraded by either of the *Pseudomonas putida* strains alone or by a single *Pseudomonas putida* strain with the plasmids which encode for the degradation of both naphthalene and camphor in an effective amount such that degradation of the aliphatic and aromatic hydrocarbons occurs.

3. The method of claim 2 wherein the aliphatic and aromatic hydrocarbons are in soil as the substrate and wherein both of the *Pseudomonas putida* strains are contacted with the soil by being mixed together with the soil and allowed to degrade the hydrocarbons.

4. The method of claim 3 wherein between about $10^3$ and $10^{10}$ cells per ml in an aqueous solution are mixed into the soil.

5. The method of claim 2 wherein the aliphatic and aromatic hydrocarbons are in an aqueous composition as the substrate and both of the *Pseudomonas putida* strains are contacted with the aqueous composition by mixing so as to degrade the hydrocarbons in the aqueous composition.

6. The method of claim 5 wherein between about $10^3$ and $10^{10}$ cells per ml of the aqueous composition are mixed in the aqueous composition.

7. The method of claim 2 wherein the ratio of *Pseudomonas putida* strains is between about 1:100 and 100:1 by cell count.

* * * * *